US00PP34904P3

(12) United States Plant Patent
Gómez Porras et al.

(10) Patent No.: US PP34,904 P3
(45) Date of Patent: Jan. 10, 2023

(54) OLIVE TREE NAMED 'I-31'

(50) Latin Name: ***Olea europaea* L.**
Varietal Denomination: I-31

(71) Applicant: Todolivo S.L., Cordova (ES)

(72) Inventors: Jose María Gómez Porras, Cordova (ES); Luis Rallo Romero, Cordova (ES); Diego Barranco Navero, Cordova (ES); Concepción Muñoz Díez, Cordova (ES); Carlos Trapero Ramírez, Cordova (ES); Pedro Valverde Caballero, Cordova (ES)

(73) Assignee: TODOLIVO S.L., Cordova (ES)

( * ) Notice: Subject to any disclaimer, the term of this patent is extended or adjusted under 35 U.S.C. 154(b) by 0 days.

(21) Appl. No.: 17/326,951

(22) Filed: May 21, 2021

(65) Prior Publication Data

US 2021/0368662 P1 Nov. 25, 2021

(51) Int. Cl.
*A01H 5/08* (2018.01)
*A01H 6/00* (2018.01)

(52) U.S. Cl.
USPC ..... Plt./158
CPC ..... *A01H 6/00* (2018.05)

(58) Field of Classification Search
USPC ..... Plt./156, 158
See application file for complete search history.

(56) References Cited

U.S. PATENT DOCUMENTS

PP22,293 P3 * 12/2011 Lavee ..... A01H 5/08
Plt./158

* cited by examiner

*Primary Examiner* — Karen M Redden
(74) *Attorney, Agent, or Firm* — Buchanan Ingersoll & Rooney P.C.

(57) ABSTRACT

A new and distinct variety of olive tree, herein referred to by its cultivar name, 'I-31', is provided which forms a upright to spreading growth habit. Fruit with a low weight and acute shape is produced. The fruit exhibit dark violet coloration and the fruit nipple is absent or weak. The stone of the fruit of the new variety is of low to medium weight, very elongated and possess a weakly rugose surface.

3 Drawing Sheets

Figure 1:
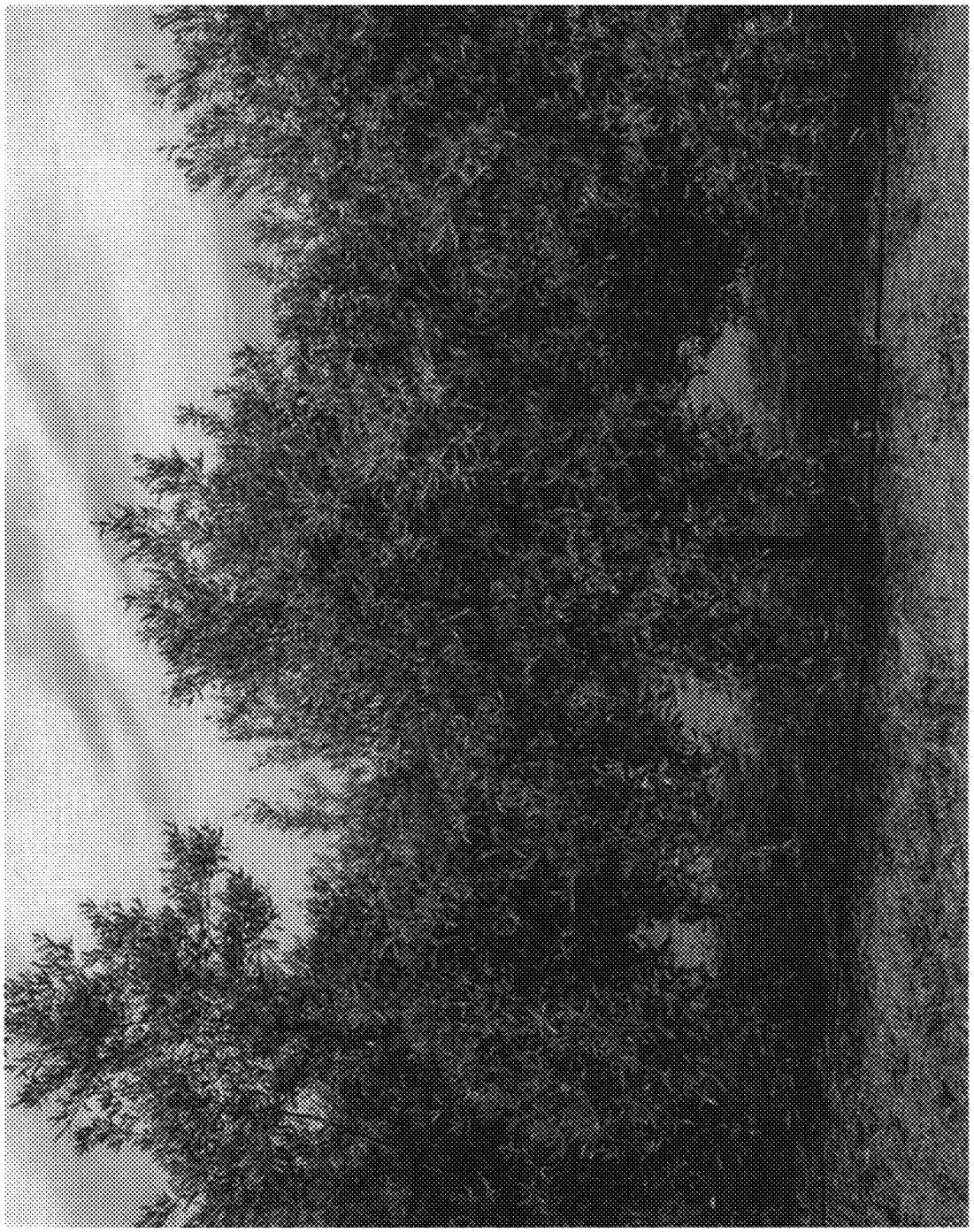

Botanical/commercial classification:
Latin name: *Oleo europaea* L.
Common name: Olive tree.
Varietal denomination: 'I-31'.

CROSS-REFERENCE TO RELATED APPLICATIONS

This application claims priority to Spanish Plant Breeder's Rights (PBR) Application No. 20205551, which was filed with the Spanish Plant Variety Office in Spain on May 21, 2020, the contents of which are hereby incorporated by reference for all purposes. This application contains a new plant variety which shares the same parental cross as the plant variety described in co-pending U.S. application Ser. No. 17/326,877. The differences between these two varieties are discussed further below.

SUMMARY OF THE INVENTION

The new variety of olive tree of the present invention was created by a controlled cross in Spain wherein two parents which previously had been studied were crossed in the hope that they would contribute the desired characteristics. The female parent (i.e., seed parent) of the new variety was the 'ARBOSANA' variety (unpatented). The male parent (i.e., pollen parent) was the 'KORONEIKI' variety (unpatented).

The parentage can be summarized as follows:

'ARBOSANA' x 'KORONEIKI'.

The seeds resulting from the above pollination were sown and small plants were obtained which were physically and biologically different from each other. Selective study resulted in the identification of a single plant of the new variety.

The new variety is larger than the 'Arbosana' variety and possesses an erect tree habit contrary to the spreading tree habit of 'Arbosana'. The new variety has an upright growth habit whereas the 'Koroneiki' variety has an open growth habit. The new variety is different from the variety described in co-pending U.S. application Ser. No. 17/326,877 in that it possesses an earlier fruit ripening period, larger fruit and a spreading to dropping growth habit. The new variety is distinguishable over similar cultivar variety 'Arbosana' because it has at least 3 point (3%) of fat yield (olive oil) in fresh in percentage, thereby having a higher quantity of olive oil percentage in its fruit than 'Arbosana'.

It was found that the new variety of the present invention possesses the following combination of characteristics:

(a) the tree has a upright to spreading growth habit
(b) the fruit weight is low and the fruit color is dark violet
(c) the fruit is acute and strongly asymmetric
(d) the fruit either possesses a weak or absent nipple
(e) the stone is very elongated with a low to medium weight and weakly rugose surface.

The new variety well meets the needs of the horticultural industry and has not been commercialized. The new variety has easy agronomic management.

The new variety can be readily distinguished from related similar varieties. The new variety possesses a medium size variety.

The new variety has been found to undergo asexual propagation in Spain by vegetative cuttings. Asexual propagation by vegetative cutting in Spain has shown that the characteristics of the new variety are stable and are strictly transmissible by such asexual propagation from one generation to another. Accordingly, the new variety undergoes asexual propagation in a true-to-type manner.

The new variety has been named 'I-31'.

BRIEF DESCRIPTION OF THE PHOTOGRAPH

The accompanying photographs show as nearly true as it is reasonably possible to make the same, in a color illustration of this character, typical specimens of the plant parts of the new variety. The accompanying photographs were taken from a specimen of the new variety that was 68 months old.

FIG. 1—illustrates the growth of the new variety.

Figure 2:
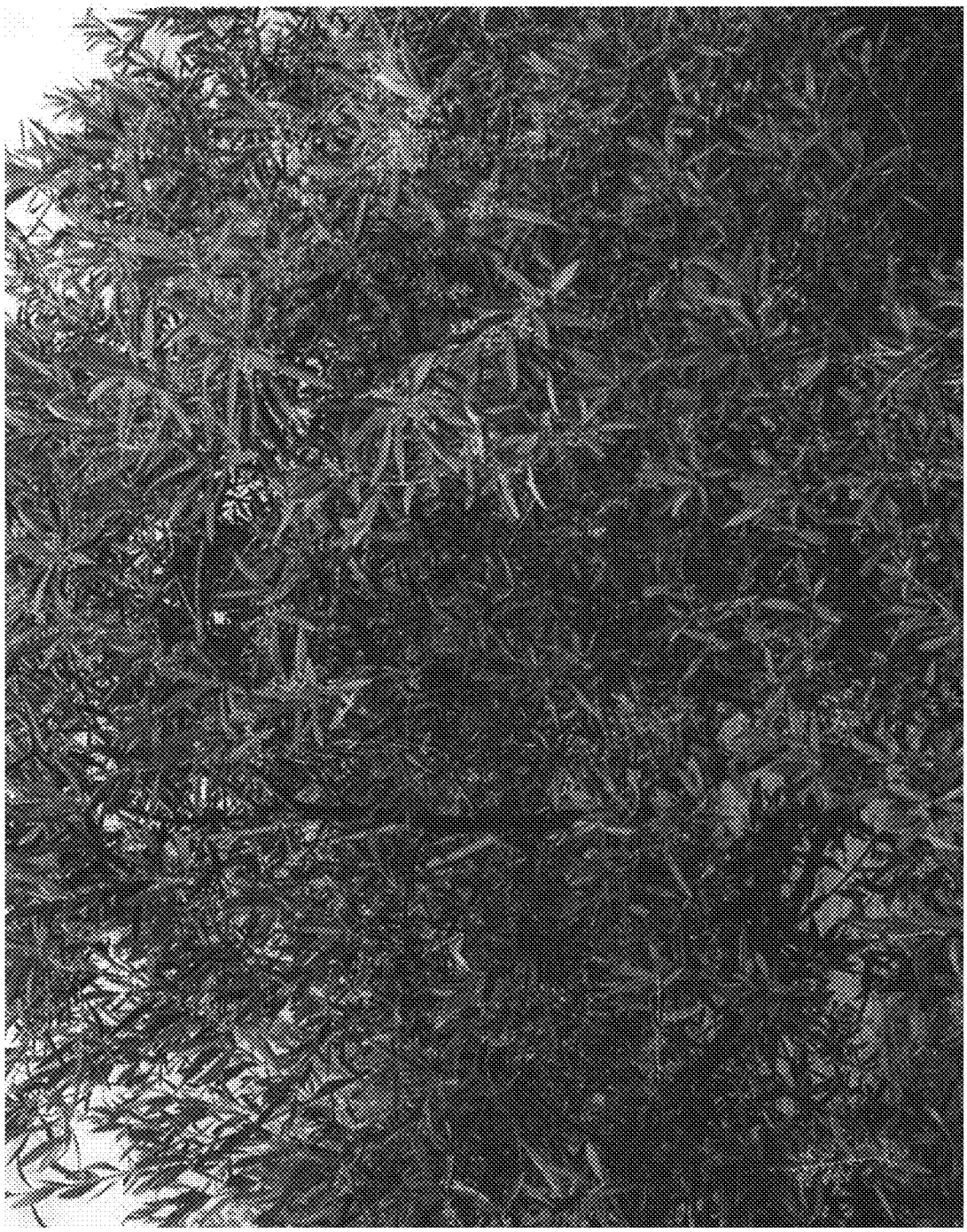

FIG. 2—illustrates the foliage of the new variety.

Figure 3:
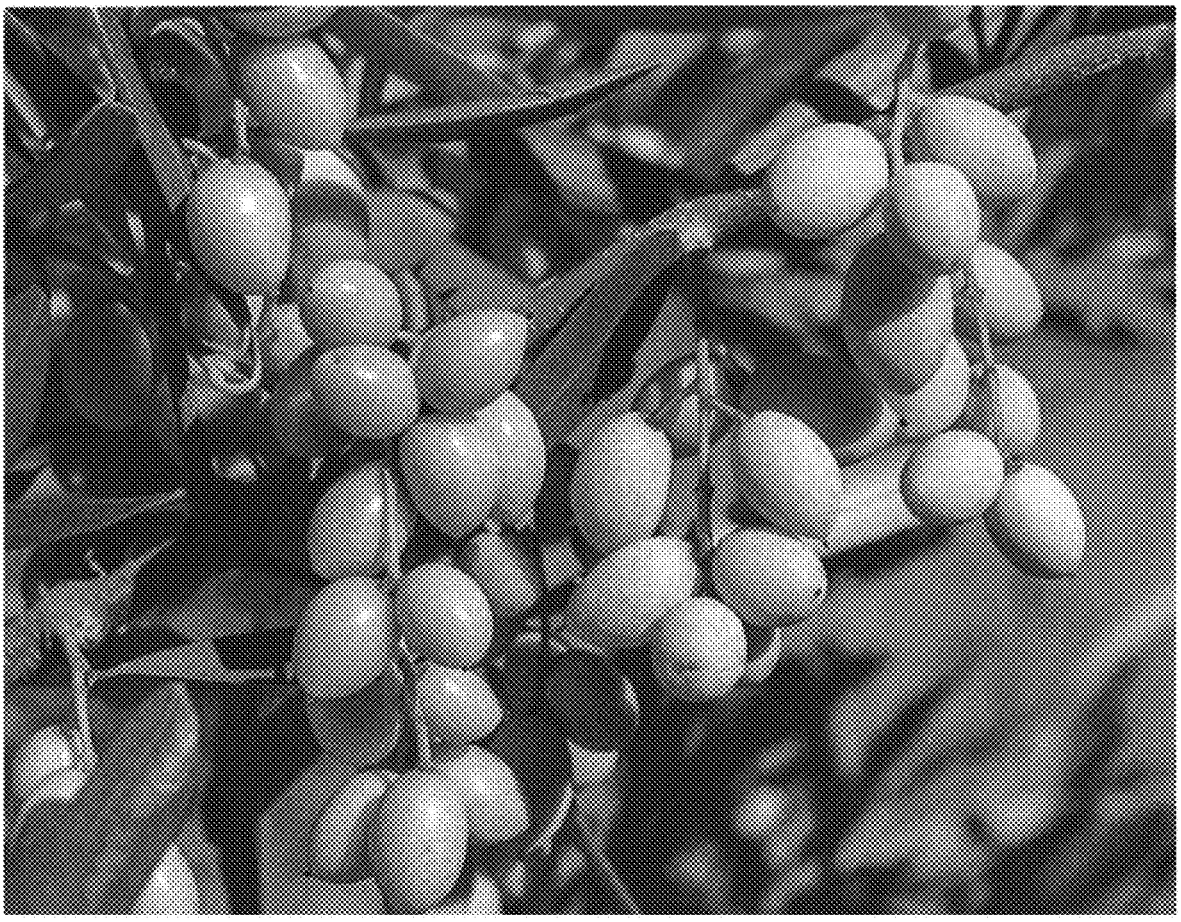

FIG. 3—illustrates specimens of the new variety's fruit.

DETAILED BOTANICAL DESCRIPTION

The chart used in the identification of the colors is that of The Royal Horticultural Society (R.H.S. Colour Chart, 2007 edition), London, England. The terminology which precedes reference to the chart has been added to indicate the corresponding coloring more common terms. The description is based on data collected from a four-year-old specimen during 2019 in Villafranca (Córdoba, Spain).

Plant:
- *Habit.*—Erect-open.
- *Growth habit.*—Upright to spreading.
- *Vigor.*—Weak.
- *Height-average.*—226 cm.
- *Width-average.*—162 cm.
- *Branching habit.*—Spreading to dropping.
- *Growth period.*—All year, less in winter or stronger in summer.

Trunk:
- *Surface texture.*—Smooth.
- *Bark color.*—Medium brown green (148C).
- *Diameter* (*average*).—62 mm.

Main stems:
- *Length* (*average*).—170 cm.
- *Amount of main branches.*—5.
- *Circumference* (*average*).—About 35 cm.
- *Color designation* (*young stems*).—Medium brown green (148C).
- *Color designation* (*mature stems*).—Medium brown green (148C).
- *Lenticels.*—Absent.
- *Internode length* (*average*).—15 cm.

Lateral branches:
- *Abundance.*—High.
- *Cross-section.*—20 cm.
- *Average length.*—80 cm.
- *Diameter* (*average*).—20 mm.
- *Internode length* (*average*).—10 cm.
- *Texture.*—Smooth.
- *Strength.*—Medium.
- *Color designation* (*young branches*).—Medium brown green (148C).
- *Color designation* (*mature branches*).—Medium brown green (148C).
- *Pubescence.*—Absent.

Leaves:
- *Arrangement.*—The arrangement of the leaves is typical of *Olea europaea* L. Species (two opposite leaves per each node).
- *Venation pattern.*—Pinnately parallel.
- *Length* (*average*).—66 mm.
- *Width* (*average*).—9.6 mm.
- *Color* (*upper surface*) *young leaves.*—Light green (142A).
- *Color* (*lower surface*) *young leaves.*—Light green (142D).
- *Color* (*upper surface*) *mature leaves.*—Medium green (143A).
- *Color* (*lower surface*) *mature leaves.*—Light green (142D).
- *Leaf margins.*—Smooth.
- *Texture.*—Smooth.

Petiole:
- *Average length.*—4 to 6 mm.
- *Average diameter.*—1 mm.

Inflorescence:
- *Type.*—Racime.
- *Average length.*—3 cm.
- *Average width.*—2 cm.
- *Number of flowers* (*average*).—At least 15.
- *Flower bud size.*—About 4 mm.
- *Flower bud shape.*—Ovate.
- *Flower bud color.*—Light green (142D).

Flower:
- *Diameter* (*average*).—5 mm.
- *Color.*—Light green (142D).

Corolla:
- *Number* (*average*).—4.
- *Length* (*average*).—3 mm.
- *Width* (*average*).—2 mm.
- *Shape.*—Elliptic.
- *Apex.*—Rounded.
- *Base.*—Fused.
- *Texture.*—Smooth.
- *Color* (*upper*).—White (155A).
- *Color* (*lower*).—White (155A).

Calyx:
- *Number* (*average*).—4.
- *Shape.*—Funnel.
- *Base.*—Fused.
- *Margin.*—Entire.
- *Texture.*—Smooth.
- *Color* (*upper*).—White (155A).
- *Color* (*lower*).—White (155A).

Pedicel:
- *Length* (*average*).—1 to 2 mm.
- *Diameter* (*average*).—1 mm.
- *Color.*—Light green (145D).

Fruit:
- *Average weight.*—Low, about 1.21 grams.
- *Shape-apex.*—Acute.
- *Color* (*flesh color*).—Dark violet (N77C).
- *Color* (*skin color*).—Black (N186A).
- *Ripening.*—Early.
- *Fat yield.*—High, 23% if fat in the fruit.
- *Size* (*average*).—Small.
- *Length* (*average*).—15 mm.

*Width* (*average*).—10 mm.
*Marbling.*—Medium.
*Symmetry.*—Asymmetric.
*Pistil scar.*—Centrate.
*Mucron.*—Present 4 (1-9 scale).
*Shape.*—Ovate.
*Apex.*—Pointed.
*Base.*—Rounded.
*Nipple.*—Light.
*Lenticels* (*average*).—2 in 1-10 scale.

Stalk:
*Length* (*average*).—5 to 10 mm.
*Diameter* (*average*).—Less than 1 mm.
*Color.*—Light green (145C).
*Depth of stalk cavity* (*average*).—1 mm.

Stone:
*Quantity.*—1.
*Shape.*—Very elongated.
*Average weight.*—Low to medium, about 0.22 grams.
*Average length.*—11 mm.
*Average width.*—8 mm.
*Grooving.*—7.
*Sutures.*—Medium.
*Color.*—Dark Green Brown (152C).
*Texture.*—Weakly rugose.
*Mucron.*—Present 4 (1-9 scale).

Development:
*Productivity.*—Very high and constant, 700 oil liter per acre and year.
*Time of flowering.*—2 weeks.
*Flowing period.*—First of May full flowering in Villafranca de Córdoba, Córdoba, Spain.
*Time of ripening.*—3 months.
*Ripening period.*—October-December in Villafranca de Córdoba, Córdoba, Spain.
*Winter hardness/cold tolerance.*—Unknown.
*Drought/heat tolerance.*—Unknown.
*Plant/fruit disease, pest resistance.*—Resistant to Cucumovirus cucumber mosaic virus (CMV), Nepovirus cherry leaf roll virus (CLRV), Incertae Sedis strawberry latent ringspot virus (SLRSV), Nepovirus arabis mosaic virus (ArMV) and leaf spot. Tolerant to Verticilium and tuberculosis.

The new 'I-31' variety has not been observed under all possible environmental conditions to date. Accordingly, it is possible that the phenotypic expression may vary somewhat with changes in light intensity and duration, cultural practices, and other environmental conditions.

We claim:

1. A new and distinct variety of olive tree named 'I-31', as illustrated and described herein.

* * * * *